(12) United States Patent
Huchel et al.

(10) Patent No.: US 8,129,569 B2
(45) Date of Patent: Mar. 6, 2012

(54) PHOTOLABILE FRAGRANCE STORAGE SUBSTANCES

(75) Inventors: Ursula Huchel, Köln (DE); Christian Kropf, Hilden (DE); Axel Griesbeck, Köln (DE); Olga Hinze, Köln (DE); Raoul Perez-Ruiz, Köln (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 12/890,796

(22) Filed: Sep. 27, 2010

(65) Prior Publication Data

US 2011/0027208 A1 Feb. 3, 2011

Related U.S. Application Data

(63) Continuation of application No. PCT/EP2009/051674, filed on Feb. 13, 2009.

(30) Foreign Application Priority Data

Mar. 28, 2008 (DE) .................. 10 2008 016 327

(51) Int. Cl.
*C07C 49/115* (2006.01)
*A61K 8/35* (2006.01)
*B05D 3/06* (2006.01)

(52) U.S. Cl. .......................... 568/327; 512/21; 424/70.1
(58) Field of Classification Search .................. 568/327; 512/21; 424/70.1
See application file for complete search history.

(56) References Cited

U.S. PATENT DOCUMENTS

| | | | |
|---|---|---|---|
| 2,686,808 | A | 8/1954 | Sprague |
| 6,949,680 | B2 | 9/2005 | Hermann |
| 2004/0259867 | A1 | 12/2004 | Fotouhi et al. |
| 2007/0264217 | A1 | 11/2007 | Dykstra et al. |
| 2008/0305063 | A1 | 12/2008 | Huchel et al. |

FOREIGN PATENT DOCUMENTS

| | | | |
|---|---|---|---|
| WO | 9323051 | A1 | 11/1993 |
| WO | 0196272 | A2 | 12/2001 |

OTHER PUBLICATIONS

Alder, K. et al. On the Condensation of Furan and Its Homologs with α,β-Unsaturated Ketones and Aldehydes. Structure of Di-, Tri- and Tetraketones of the Fatty Series, German Chemical Society, vol. 76, No. 3, 1943, pp. 183-205.

Neckers, Douglas C. "Development Photochemistry. The Norrish Type II Reaction." J. Org. Chem., vol. 36, No. 13, 1971, pp. 1838-1840.
Brown et al. "Reaction of Organoboranes with alpha-Bromo Ketones under the Influence of Potassium t-Butoxide in Tetrahydrofuran. A New Technique for the alpha Alkylation of Keytones." Journal of the American Chemical Society, vol. 90, No. 22, Oct. 1968, pp. 6218-6219.
Xiao Zhuanquan et al. "Synthesis of Endo-alpha-isocamphanyl Keytones and Beta-isocamphanyl Alcohols," Chemistry and Industry of Forest Products, vol. 16, No. 3, Sep. 1996, pp. 19-22.
Dias-Marrero et al. "Caminatal, an aldehyde sesterterpene with a novel carbon skeleton from the Antarctic sponge *Suberites caminatus*." Tetrahedron Letters, vol. 44, 2003, pp. 5939-5942.
Iwasawa et al. "Synthesis of Medium-Sized Bicyclic Compounds by Intramolecular Cyclization of Cyclic Beta-Keto Radicals Generated from Cyclopropanols Using Manganese (III) Tris (pyridine-2-carboxylate) and Its Application to Total Synthesis of 10-Isothiocyanatoguaia-6-ene." Bulletin Chem. Soc. Jpn., vol. 72, No. 1, 1999, pp. 85-97.
Quinkert, G. et al. "Keten Formation by Intramolecular Disproportionation of Photochemically Produced Alkyl-Acyl-Radical Pairs from Cyclic Ketones," Tetrahedrom letters, vol. 6, 1962, pp. 221-225.
Hwu et al. "The Trimethylsilyl Cationic Species as a Bulky Proton. Application to Chemoselective Dioxolanation." Journal of Organic Chemistry, vol. 50, No. 20, 1985, pp. 3946-3948.
Croft et al. "The chemistry of *Eremophila* spp. XXI. Structural study of a new eremane diterpene." Database caplus Online Chemical Abstracts service, May 13, 2009, XP002527604, Database Accession No. 1984: 451700 Abstract.
Croft et al. "The Chemistry of *Eremophila* ssp. XXI: Structural Study of a New Eremane Diterpene" Aust. J. Chem., vol. 37, Apr. 1984, pp. 785-793.
Arctander, S. Perfume and Flavor Chemicals (Aroma Chemicals), vol. 2, 1969.
J. March, Advanced Organic Chemistry, 4. Aufl. S. 783-789.tif, (2001).
Jun, Chul-Ho et al. "Direct Synthesis of Ketones from Primary Alcohols and 1 Alkenes." Applied Chemistry, International Edition, vol. 37, No. 1/2, 1998, pp. 145-147.
Iwasawa et al. "Synthesis of Medium-Sized Bicyclic Compounds by Intramolecular Cyclization of Cyclic Beta-Keto Radicals Generated from Cyclopropanols Using Manganese (III) Tris(2-pyridinecarboxylate)." Chemistry Letters, 1993, pp. 545-548.
Kiyooka et al. Enaminone Intermediate in the One-Methylene Incorporated Dimerization Reaction of Ketone Enolate. Chemistry Letters (1987), (9), 1775-1778.
Neckers, D. et al., "Developmental Photochemistry. The Norrish Type II Reaction", J. Org. Chem., vol. 36, No. 13, 1971, pp. 1838-1840.

*Primary Examiner* — Sikarl Witherspoon
(74) *Attorney, Agent, or Firm* — David P. LeCroy

(57) ABSTRACT

Photolabile fragrance storage substances capable of the photo-induced release of cyclic compounds having semi-cyclic double bonds are described. Further described is a method for sustained scenting of surfaces and a method for production of said fragrance storage substances.

11 Claims, No Drawings

PHOTOLABILE FRAGRANCE STORAGE SUBSTANCES

CROSS REFERENCE TO RELATED APPLICATIONS

The present application is a continuation of PCT/EP2009/051674 filed 13 Feb. 2009, which claims priority to German Patent Application No. 10 2008 016 327.9 filed 28 Mar. 2008, both of which are incorporated herein by reference.

Textile-treatment, surface-treatment and cosmetic agents often contain scents that impart a pleasant and fresh odor to the agents. The scents, which can be both synthetic and natural in nature, usually mask the inherent scent note of other ingredients, thus producing a positive odor impression in the consumer.

In washing agents, scents are particularly important constituents of the composition, since it is desirable that laundry have a pleasant and fresh smell both when wet and when dry. A fundamental problem in using scents is their volatility, since otherwise a scent effect could not be achieved. The difficulty with using scents in washing and cleaning agents as well as cosmetic agents, is that the scents are volatile compounds; however, it is desirable to produce a long-lasting scent effect that is as consistent as possible. In addition, the scent impression of a perfume changes over time, as fragrances representing the fresh and light notes of the perfume volatilize more quickly than scents representing the middle and base notes.

Approaches to solving this problem include applying scents onto carrier materials and coating the scented carriers, or encapsulating scents or incorporating them into compounds (for example, cyclodextrin-perfume complexes). A further possibility is chemically bonding the scents to carrier media; the chemical bond is slowly broken and the scent released as a result. This kind of carrier-bound precursor form of a scent is also known as a "pro-fragrance" or scent storage substance. In this connection, International Patent Application Publication No. WO 2007/087977 discloses the use of 1-aza-3,7-dioxabicyclo[3.3.0]octane compounds as scent storage substances for delayed release of scent aldehydes and scent ketones by hydrolysis. An alternative possibility for delayed release of scents involves use of so-called photoactivatable substances as scent storage substances. The action of sunlight or another electromagnetic radiation source of a specific wavelength induces breakage of a covalent bond in the scent storage substance molecule, thereby releasing a scent. For effective release of the scent, the above-described process must tolerate the presence of oxygen and water.

In this connection, U.S. Pat. No. 6,949,680 discloses the use of specific phenyl ketones or pyridyl ketones as photoactivatable substances that, in a photochemical fragmentation, release a terminal alkene as an active substance in the presence of light. The aforesaid active substance possesses, for example, a scent-imparting or antimicrobial activity that is at first delayed by the photochemically induced decomposition, and over a longer period of time released on a specific surface. The aforesaid photolabile phenyl or pyridyl ketones constituting scent storage substances are manufactured in a complex, multi-step synthesis method using protecting-group operations wherein the synthesis must be individually adapted for each individual active substance. U.S. Pat. No. 6,949,680 also does not disclose photo-induced release of cyclic alkenes having a semicyclic double bond as active substances, or the manufacture or use of the corresponding scent storage substances. Cyclic alkenes having a semicyclic double bond, which can involve, for example, the olfactorily significant class of the cyclic terpenes having a semicyclic double bond, represent an important class of odor compounds. They can, for example, contribute to imparting a pleasant and fresh odor to textile- and surface-treatment agents, or to cosmetic agents. The aforesaid alkenes are as a rule notable for their high vapor pressure, and because of their low degree of functionalization are difficult to bond chemically to conventional carrier media. In addition, no photoactivatable substances that can release the aforesaid alkenes over a longer period of time are known.

The present invention therefore is directed towards photoactivatable substances containing scent storage substances and that permit delayed release of cyclic alkenes having a semicyclic double bond, particularly cyclic terpenes or cyclic terpenoids having a semicyclic double bond. The present invention also provides a simple, economical, and convergent synthesis method for manufacturing the aforesaid scent storage substances.

It has now surprisingly been found that certain cyclic phenyl ketones containing photoactivatable scent storage substances permit the delayed release of cyclic alkenes having a semicyclic double bond. Accordingly, the present invention is directed towards a ketone of the general formula (I)—

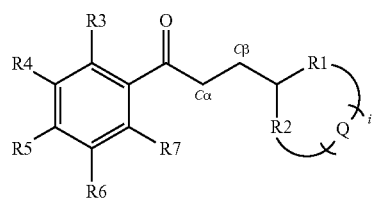

Formula (I)

wherein i=1 or 2; R3, R4, R5, R6, and R7 are independently hydrogen, a halogen atom, NO$_2$, a linear or branched, substituted or unsubstituted alkoxy group having 1 to 15 carbon atoms, or a linear or branched, substituted or unsubstituted alkyl group having 1 to 15 carbon atoms; R1 and R2 are independently a secondary, tertiary, or quaternary carbon atom; and Q is at least one divalent substituted or unsubstituted group having 1 to 10 carbon atoms and bridging R1 and R2.

The term "secondary carbon atom" is to be understood for purposes of the invention as a carbon atom that is covalently bonded to two further carbon atoms. The term "tertiary carbon atom" or "quaternary carbon atom" is to be understood for purposes of the invention as a carbon atom that is covalently bonded, respectively, to three or four further carbon atoms.

In a particularly preferred embodiment of the invention, R1 and R2 are each independently a secondary or tertiary carbon atom. In a very particularly preferred embodiment of the invention, one of the two residues R1 and R2 is a secondary carbon atom, while the other residue is a tertiary carbon atom.

A further subject of the invention is a composition such as a washing or cleaning agent (preferably a textile- or surface-treatment agent) or a cosmetic agent containing at least one ketone according to general formula (I) as defined above, wherein the ketone is present in an amount of from 0.001 to 5 wt %, advantageously from 0.01 to 4 wt %, with further advantage from 0.1 to 3 wt %, particularly from 0.5 to 2 wt %, based on total amount of the composition.

A further subject of the present invention is a method for long-lasting scenting of surfaces, wherein a ketone according to the present invention of the general formula (I) or a composition according to the present invention containing such a ketone is applied onto a surface to be scented, with the surface then exposed to an electromagnetic radiation of wavelengths from 200 to 400 nm. Natural sunlight can preferably be regarded as an electromagnetic radiation for purposes of the present invention.

The present invention also provides a method for manufacturing a ketone according to the present invention of general formula (I), comprising the following steps:

a) producing organoborane adducts by hydroboration of a compound of general formula (III)

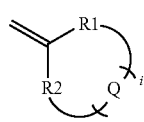

Formula (III)

wherein i=1 or 2, R1 and R2 are each independently a secondary, tertiary, or quaternary carbon atom, and Q is at least one divalent substituted or unsubstituted group having 1 to 10 carbon atoms and bridging R1 and R2, and b) reacting the organoborane adducts generated in step a) with a compound of general formula (IV)

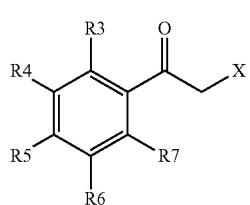

Formula (IV)

where X is a halogen atom and R3, R4, R5, R6, and R7, mutually independently, denote hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms, thereby producing a compound according to general formula (I).

The present invention also provides for use of a ketone according to the present invention of the general formula (I) as a scent storage substance, and use of a ketone according to the present invention in liquid or solid washing agents, fabric softeners, softening washing agents, washing adjuvants, or cosmetic agents for treating skin and hair.

Likewise the present invention includes use of ketones according to the present invention, particularly compositions according to the present invention such as washing or cleaning agents or cosmetic agents to improve scent yield, particularly on textiles.

Ketones according to the present invention of the general formula (I) wherein i=2 and at least one of the divalent substituted or unsubstituted groups Q bridging R1 and R2 contains 2 to 6 carbon atoms is preferred for purposes of the invention.

Ketones according to the present invention of the general formula (I) wherein i=2 and one of the divalent groups Q bridging R1 and R2 is unbranched and contains 2, 3, or 4 carbon atoms, preferably 3 or 4 carbon atoms, is particularly preferred.

Likewise preferred are ketones according to the present invention of the general formula (I) wherein i=2 and one of the divalent groups Q bridging R1 and R2 contains from 2, 3, or 4 carbon atoms, respectively, covalently linked to one another. Very particularly preferred for purposes of the invention is a ketone according to the present invention of the general formula (I) wherein i=2 and one of the divalent groups Q bridging R1 and R2 is unbranched and contains 2, 3, or 4 carbon atoms, in particular 3 or 4 carbon atoms, while the other divalent group Q bridging R1 and R2 is branched, and the shortest direct connection between R1 and R2 is made up of 2, 3, or 4 carbon atoms respectively covalently linked to one another.

Likewise preferred for purposes of the invention are ketones according to the present invention of the general formula (I) wherein R1 and/or R2 and/or at least one divalent group Q bridging R1 and R2 has a substitution with at least one heteroatom chosen from N, O, or S. Ketones according to the present invention of the general formula (I) wherein R1 and/or R2 and/or at least one divalent group Q bridging R1 and R2 has a substitution in the form of an —OH, —OR$^a$, —SH, —SR$^b$, or —NR$^c$R$^d$ group, where R$^a$, R$^b$, R$^c$, and R$^d$ are selected, mutually independently, from hydrogen and branched or unbranched, substituted or unsubstituted alkyl groups containing 1 to 10, particularly 1 to 4, and particularly preferably 1, 2, or 3 carbon atoms, is particularly preferred.

Likewise particularly preferred are ketones according to the present invention of the general formula (I) in which a divalent group Q bridging R1 and R2 comprises a ketone structure, carboxylic-acid structure, lactone structure, amide structure, ester structure, and/or aldehyde structure.

Also preferred are ketones according to the present invention of the general formula (I) in which four of the five aryl substituents R3, R4, R5, R6, and R7 are hydrogen. R3, R4, R6, and R7 are preferably hydrogen, while the substituent in the R5 para-position is a halogen atom, particularly —F, —Cl, or —Br, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 is —Cl, —Br, —$NO_2$, or an alkyl or alkoxy group comprising 1 to 4 carbon atoms. By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group.

Substitution in the para-position (R5) is particularly preferred because the electron structure of the aromatic ring can be most effectively modified here, with the result that maximum absorption of ketones of the general formula (I) can easily be adapted to a specific wavelength.

Likewise preferred is a ketone according to the present invention of the general formula (I) in which R3, R4, R5, R6, and R7 are hydrogen.

Further preferred for purposes of the invention are ketones according to the present invention of the general formula (I) from which, by cleavage of the Cα-Cβ bond, ketones of the general formula (II)

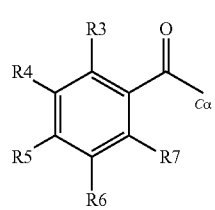

Formula (II)

and compounds of the general formula (III)

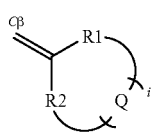

Formula (III)

are formed, wherein i=1 or 2; R3, R4, R5, R6, and R7 are each independently hydrogen, a halogen atom, NO$_2$, a linear or branched, substituted or unsubstituted alkoxy group having 1 to 15 carbon atoms or a linear or branched, substituted or unsubstituted alkyl group having 1 to 15 carbon atoms; R1 and R2 are each independently a secondary, tertiary, or quaternary carbon atom; and Q is at least one divalent substituted or unsubstituted group having 1 to 10 carbon atoms and bridging R1 and R2.

In a particularly preferred embodiment of the invention, R1 and R2 in formula (III) are mutually and independently a secondary or tertiary carbon atom. In a very particularly preferred embodiment of the invention, one of the two residues R1 and R2 is a secondary carbon atom, while the respective other reside is a tertiary carbon atom.

A compound according to the present invention of general formula (II) in which four of the five aryl substituents R3, R4, R5, R6, and R7 are hydrogen is preferred. By preference, R3, R4, R6, and R7 are hydrogen, while the substituent in the R5 para-position is a halogen atom, NO$_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 is —Cl, —Br, —NO$_2$, or an alkyl or alkoxy group comprising 1 to 4 carbon atoms.

By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group.

Ketones according to the present invention of general formula (I) from which proceeds, by cleavage of the Cα-Cβ bond, a compound of the general formula (III) wherein i=2 and at least one of the divalent substituted or unsubstituted groups Q bridging R1 and R2 comprises 2 to 6 carbon atoms is preferred for purposes of the invention. Particularly preferred in this context is a compound of the general formula (III) wherein i=2 and one of the divalent groups Q bridging R1 and R2 is unbranched and comprises 2, 3, or 4 carbon atoms, in particular 3 or 4 carbon atoms. Likewise preferred is a compound of general formula (III) wherein i=2 and one of the divalent groups Q bridging R1 and R2 is branched, and the shortest direct connection between R1 and R2 is constituted from 2, 3, or 4 carbon atoms respectively covalently linked to one another. Very particularly preferred for purposes of the invention is a ketone according to the present invention of general formula (I) from which proceeds, by cleavage of the Cα-Cβ bond, a compound of general formula (III) wherein i=2 and one of the divalent groups Q bridging R1 and R2 is unbranched and encompasses 2, 3, or 4 carbon atoms, in particular 3 or 4 carbon atoms, while the other divalent group Q bridging R1 and R2 is branched, and the shortest direct connection between R1 and R2 is constituted from 2, 3, or 4 carbon atoms respectively covalently linked to one another.

Likewise preferred for purposes of the invention is a compound of the general formula (III) wherein R1 and/or R2 and/or at least one divalent group Q bridging R1 and R2 has a substitution with at least one heteroatom chosen from N, O, or S. A compound of the general formula (III) wherein R1 and/or R2 and/or at least one divalent group Q bridging R1 and R2 has a substitution in the form of an —OH, —OR$^a$, —SH, —SR$^b$, or —NR$^c$R$^d$ group, where R$^a$, R$^c$, and R$^d$ are selected, mutually independently, from the group made up of hydrogen and branched or unbranched, substituted or unsubstituted alkyl groups comprising 1 to 10 carbon atoms, is particularly preferred.

Likewise particularly preferred is a compound of the general formula (III) wherein a divalent group Q bridging R1 and R2 comprises a ketone structure, carboxylic-acid structure, lactone structure, amide structure, ester structure, and/or aldehyde structure.

Also preferred is a compound of the general formula (III) which is a cyclic terpene or cyclic terpenoid having a semicyclic double bond.

The term "semicyclic double bond" is to be understood for purposes of the invention as a double bond between two carbon atoms wherein the one carbon atom of the double bond assumes an exocyclic position, while the other carbon atom of the double bond is part of a ring system.

The drawing (B-I) below is intended to further explain the concept of the semicyclic double bond:

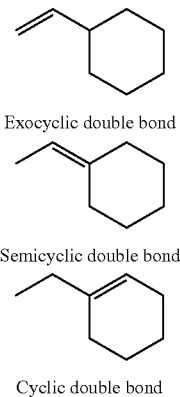

Drawing (B-I)

Exocyclic double bond

Semicyclic double bond

Cyclic double bond

"Terpenes" are to be understood according to the present invention as natural substances constructed from isoprene basic units and derivatives.

"Terpenoids" are to be understood according to the present invention as natural substances constructed from isoprene basic units and derivatives, and that have a high degree of structural affinity with the terpenes but differ from them, for example, by loss or rearrangement of a fragment, preferably of a methyl group.

Depending on the number of basic units, terpene units are classified as monoterpenes, sesquiterpenes, diterpenes, sesterpenes, triterpenes, and tetraterpenes.

According to a preferred embodiment of the invention, monocyclic monoterpenes, bicyclic monoterpenes, and cyclic sesquiterpenes are particularly in accordance with the present invention. All terpenes according to the present invention encompass at least one semicyclic double bond whose exocyclic carbon atom, prior to cleavage of the Cα-Cβ bond, is covalently linked to the Cα atom in the ketone according to the present invention of the general formula (I).

Particularly preferred cyclic terpenes or cyclic terpenoids having a semicyclic double bond include β-phellandrene (p-mentha-1(7),2-diene), α-fenchene (7,7-dimethyl-2-methylenebicyclo[2.2.1]heptane), β-fenchene (2,2-dimethyl-5-methylenebicyclo-[2.2.1]heptane), camphene (2,2-dimethyl-3-methylenebicyclo[2.2.1]heptane), sabinene (4-methylene-1-(1-methylethyl)bicyclo-[3.1.0]hexane), pinocarveol, β-pinene (6,6-dimethyl-2-methylenebicyclo-[3.1.1]heptane), trichodiene (1,4-dimethyl-4-(1-methyl-2-methylenecyclopentyl)cyclohexene), β-humulene (1E,5E)-1,4,4-trimethyl-8-methylenecycloundeca-1,5-diene, or γ-humulene (1E,6E)-1,8,8-trimethyl-5-methylenecycloundeca-1,6-diene. Also particularly preferred are all possible enantiomers or diastereomers of the aforesaid cyclic terpenes or cyclic terpenoids having a semicyclic double bond.

The aforesaid cyclic terpenes or cyclic terpenoids having a semicyclic double bond are generally notable for a high tendency toward isomerization. Long exposure to sunlight can result in skeleton rearrangements (e.g., as a result of Wagner-Meerwein rearrangements) or in the formation of double-bond isomers. This is undesirable, since the aforesaid isomers often differ considerably in terms of odor impression from the cyclic terpenes or cyclic terpenoids having a semicyclic double bond that are originally present. In some circumstances, the scent impression of a multi-component perfume oil mixture can be decisively modified as a result. An advantage of the present invention is therefore the fact that the terpenes or terpenoids according to the present invention are only released directly upon utilization, as a result of sunlight exposure, with the result that a change in scent due to previous isomerization reactions can be almost ruled out.

The subject of the present invention is likewise a composition containing at least one compound of the general formula (Ia)—

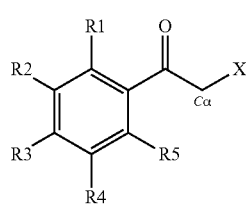

Formula (Ia)

where R1, R2, R3, R4, and R5 are mutually and independently hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms, and X is, after cleavage of the Cα-X bond, a cyclic compound containing at least one semicyclic double bond, the exocyclic carbon atom of the semicyclic double bond being covalently linked before cleavage of the Cα-X bond to the Cα atom.

In a particularly preferred embodiment, the residue X after cleavage of the Cα-X bond is a cyclic terpene having a semicyclic double bond, by preference chosen from β-phellandrene (p-mentha-1(7),2-diene), α-fenchene (7,7-dimethyl-2-methylenebicyclo[2.2.1]heptane), β-fenchene (2,2-dimethyl-5-methylenebicyclo-[2.2.1]heptane), camphene (2,2-dimethyl-3-methylenebicyclo[2.2.1]heptane), sabinene (4-methylene-1-(1-methylethyl)bicyclo-[3.1.0]hexane), pinocarveol, β-pinene (6,6-dimethyl-2-methylenebicyclo-[3.1.1]heptane), trichodiene (1,4-dimethyl-4-(1-methyl-2-methylenecyclopentyl)cyclohexene), β-humulene (1E,5E)-1,4,4-trimethyl-8-methylenecycloundeca-1,5-diene, or γ-humulene (1E,6E)-1,8,8-trimethyl-5-methylenecycloundeca-1,6-diene. Also particularly preferred are all possible enantiomers or diastereomers of the aforesaid cyclic terpenes or cyclic terpenoids having a semicyclic double bond.

A compound according to the present invention of the general formula (Ia) in which four of the five aryl substituents R3, R4, R5, R6, and R7 are hydrogen is preferred. R3, R4, R6, and R7 preferably are hydrogen, while the substituent in the R5 para-position is a halogen atom, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 is —Cl, —Br, —$NO_2$, or an alkyl or alkoxy group comprising 1 to 4 carbon atoms. By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group.

In a preferred embodiment of the invention, the composition (e.g., a washing or cleaning agent or cosmetic agent) according to the present invention contains at least one further scent. The scents or perfume oils preferably used are subject to no limitations at all. For example, synthetic or natural fragrance compounds of the ester, ether, aldehyde (scent aldehyde), ketone (scent ketone), alcohol, hydrocarbon, acid, carbonic acid ester, aromatic hydrocarbon, aliphatic hydrocarbon, saturated and/or unsaturated hydrocarbon types, and mixtures thereof, can be used by preference as scents.

All usual scent aldehydes and scent ketones typically used to bring about a pleasant scent sensation can be used in this context as scent aldehydes or scent ketones. Suitable scent aldehydes and scent ketones are known to the skilled artisan. The scent ketones can encompass all ketones that can impart a desired scent or a fresh sensation. Mixtures of different ketones can also be used. Usable ketones include alpha-damascone, delta-damascone, isodamascone, carvone, gamma-methyl ionone, Iso-E-Super, 2,4,4,7-tetramethyl-oct-6-en-3-one, benzylacetone, beta-damascone, damascenone, methyldihydrojasmonate, methyl cedrylone, hedione, and mixtures thereof. Suitable scent aldehydes can be any aldehydes that, correspondingly to the scent ketones, convey a desired scent or a fresh sensation. These can once again be individual aldehydes or aldehyde mixtures. Suitable aldehydes include melonal, triplal, ligustral, adoxal, lilial, etc. The scent aldehydes and scent ketones have an aliphatic, cycloaliphatic, aromatic, ethylenically unsaturated structure, or a combination of said structures. In addition, further heteroatoms or polycyclic structures can be present. The structures can comprise suitable substituents such as hydroxyl or amino groups. For further suitable scents selected from aldehydes and ketones, reference is made to the work of Steffen Arctander published 1960 and 1969 respectively, reprinted 2000; ISBN: Aroma Chemicals Vol. 1: 0-931710-37-5, Aroma Chemicals Vol. 2: 0-931710-38-3. Suitable scents of the ester type include benzyl acetate, phenoxyethylisobutyrate, p-tert-butylcyclohexyl acetate, etc. Fragrance compounds of the hydrocarbon type include terpenes such as limonene and pinene. Suitable scents of the ether type include benzyl ethyl ether and ambroxan. Suitable scent alcohols include 10-undecen-1-ol, 2,6-dimethylheptan-2-ol, 2-methylbutanol, 2-methylpentanol, 2-phenoxyethanol, 2-phenylpropanol, etc. Scents or perfume oils can also be natural fragrance mixtures such as those accessible from plant sources. The scents or perfume oils can also be essential oils such as angelica oil, anise oil, arnica flower oil, etc.

The amount of the at least one scent in the preparation according to the present invention (e.g., a washing or cleaning agent or cosmetic agent) is preferably from 0.001 to 5 wt %, advantageously from 0.01 to 4 wt %, with further advantage from 0.1 to 3 wt %, and very particularly preferably from 0.5 to 2 wt %, based on total amount of the preparation. Preferably, mixtures of different scents (from the different aforementioned scent classes) are used that together produce an attractive scent note. In this case the total mass of the scent mixtures, based on the total mass of the preparation, corresponds to the total quantity of the at least one scent in the preparation according to the present invention.

In a further preferred embodiment of the invention, the preparation according to the present invention is a textile- or surface-treatment agent, the aforesaid agents greatly preferably additionally containing at least one surfactant chosen from anionic, cationic, nonionic, zwitterionic, amphoteric surfactants, or mixtures thereof.

In another preferred embodiment of the invention, the preparation according to the present invention is a textile-treatment agent in the form of a washing agent, fabric softener, softening washing agent, or washing adjuvant.

Preferably, the ketone according to the present invention of the general formula (I), or the mixture of different ketones according to the present invention of the general formula (I), is present in the preparation according to the present invention in the form of a washing agent, fabric softener, softening washing agent, or washing adjuvant in amounts of from 0.001 to 5 wt %, advantageously from 0.01 to 4 wt %, with further advantage from 0.1 to 3 wt %, in particular from 0.5 to 2 wt %, each based on total amount of the preparation.

A composition containing at least one ketone according to the present invention of the general formula (I), the aforesaid composition being a textile- or surface-treatment agent, by preference a washing agent, fabric softener, washing adjuvant, or cleaning agent, the aforesaid ketone being contained by preference in amounts of from 0.001 to 5 wt %, advantageously from 0.01 to 4 wt %, with further advantage from 0.1 to 3 wt %, in particular from 0.5 to 2 wt %, each based on total amount of the preparation, is thus a further subject of the invention.

The textile-treatment agent can be solid or liquid, with liquid washing agents being preferred. When the agent according to the present invention is a washing agent, preferably it contains at least one surfactant chosen from anionic, nonionic, zwitterionic, and amphoteric surfactants. When the agent according to the present invention is a softening washing agent ("2 in 1"), preferably it contains a softening component as well as at least one surfactant chosen from anionic, nonionic, zwitterionic, and amphoteric surfactants. Washing adjuvants are used for targeted pretreatment of the laundry before washing, in a context of spots or heavy staining. Washing adjuvants include, for example, pretreatment agents, soaking agents, decolorants, and spot remover.

When the agent according to the present invention is a fabric softener, it preferably contains a softening component. Fabric softeners are preferred as agents according to the present invention because they come into contact with the textiles only in the last step of a conventional textile washing operation (the rinse cycle), and a quantity of scents that is large as possible can thus absorb onto the textile with no risk that the scents will be removed again in subsequent steps. It is very particularly preferred that the softening component be an alkylated quaternary ammonium compound, at least one alkyl chain being interrupted by an ester group or amido group. The softening component includes quaternary ammonium compounds such as monoalk(en)yltrimethylammonium compounds, dialk(en)yldimethylammonium compounds, mono-, di- or triesters of fatty acids with alkanolamines. Further softening components usable according to the present invention include quaternized protein hydrolysates or protonated amines. Cationic polymers are also suitable softening components. Also usable are polyquaternized polymers (e.g., Luviquat® Care of BASF), as well as chitin-based cationic biopolymers and derivatives thereof, for example, the polymer obtainable under the commercial designation Chitosan® (manufacturer: Cognis). Further suitable softening components include protonated or quaternized polyamines. Particularly preferred softening components are alkylated quaternary ammonium compounds of which at least one alkyl chain is interrupted by an ester group and/or amido group. N-Methyl-N-(2-hydroxyethyl)-N,N-(ditallowacyloxyethyl)ammonium methosulfate or bis-(palmitoyloxyethyl)hydroxyethylmethylammonium methosulfate are very particularly preferred. Preparations according to the present invention in the form of fabric softeners can also contain nonionic softening components such as polyoxyalkylene glycerol alkanoates, polybutylenes, long-chain fatty acids, ethoxylated fatty acid ethanolamides, alkyl polyglucosides, particularly sorbitan mono-, di-, and triester, and fatty acid esters of polycarboxylic acids. In the fabric softener according to the present invention comprising a preparation according to the present invention, the softening component is present advantageously in amounts from 0.1 to 80 wt %, usually 1 to 40 wt %, by preference 2 to 20 wt %, and in particular 3 to 15 wt %, and the at least one scent or the mixture of different scents is present in amounts advantageously from 0.1 to 20 wt %, by preference 1 to 13 wt %, and in particular 2 to 8 wt %, each based on total amount of the agent according to the present invention.

The preparation according to the present invention in the form of a fabric softener can optionally contain, as a further component, one or more nonionic surfactants. Those typically utilized in washing agents can also be used.

It is further preferred that the preparation according to the present invention in the form of a textile- or surface-treatment agent additionally contain further advantageous ingredients that are known to the skilled artisan. Compositions according to the present invention in the form of a textile-treatment agent can, for example, in addition to the surfactants and/or softening compounds, contain additional ingredients that further improve the applications-engineering and/or aesthetic properties of the textile-treatment agent. In the context of the present invention, preferred textile-treatment agents additionally contain one or more substances from the group of detergency builders, bleaching agents, bleach activators, enzymes, electrolytes, nonaqueous solvents, pH adjusting agents, perfumes, perfume carriers, fluorescing agents, dyes, hydrotopes, foam inhibitors, silicone oils, antiredeposition agents, optical brighteners, anti-gray agents, shrinkage preventers, wrinkle-prevention agents, color transfer inhibitors, antimicrobial active substances, germicides, fungicides, antioxidants, preservatives, corrosion inhibitors, antistatic agents, bittering agents, ironing adjuvants, proofing and impregnation agents, swelling and anti-slip agents, neutral filler salts, and UV absorbers. Silicates, aluminum silicates (in particular zeolites), carbonates, salts of organic di- and polycarboxylic acids, and mixtures of said substances may be recited, in particular, as detergency builders that can be present in the textile-treatment agents.

Production of fabric softeners comprising a textile-treatment agent can be obtained in accordance with techniques familiar to the skilled artisan for manufacturing fabric softeners. This can be accomplished, for example, by mixing the raw materials, if applicable with the use of high-shear mixing apparatuses. Melting of the softening component(s) and subsequent dispersion of the melt in a solvent, preferably water, is recommended. The additional ingredients can be integrated by simple mixing into the fabric softener. Manufacture of the liquid washing agent comprising a textile-treatment agent is accomplished by means of usual and known methods and processes wherein, for example, the constituents are simply mixed in agitator vessels; usefully, water, nonaqueous solvents, and surfactants are made ready and the further constituents are added. Separate heating during manufacture is not necessary; if desired, the temperature of the mixture should not exceed 80° C.

As a surface treatment agent, the preparation according to the present invention can be used to clean hard surfaces. This can refer, for example, to dishwashing agents that are used for manual or automatic cleaning of tableware. It can also involve usual industrial or household cleaners with which hard surfaces such as furniture surfaces, floor tiles, wall tiles, and wall and floor coverings are cleaned. Possible hard surfaces are not only tableware but also all other hard surfaces, in particular made of glass, ceramic, plastic, or metal, in the home and commercially. The textile- or surface-treatment agents can be solid or liquid formulations; solid formulations can exist as a powder, granulate, extrudate, in tab form, as a tablet, or as a pressed and/or melted shaped element. Liquid formulations can be solutions, emulsions, dispersions, suspensions, microemulsions, gels, or pastes. As a surface-treatment agent, the agent can correspondingly contain usual ingredients of cleaning agents in usual quantities.

In a further preferred embodiment of the invention, preparations according to the present invention include cosmetic agents for treating skin and hair. By preference, the ketone or mixture of different ketones according to the present invention of general formula (I) is present in the preparation according to the present invention in the form of a cosmetic agent for treating skin and hair in amounts of from 0.001 to 5 wt %, advantageously from 0.01 to 4 wt %, with further advantage from 0.1 to 3 wt %, in particular from 0.5 to 2 wt %, each based on total weight of preparation. A cosmetic agent for treating skin and hair containing at least one ketone according to the present invention of general formula (I) in an amount of from 0.001 to 5 wt %, advantageously from 0.01 to 4 wt %, with further advantage from 0.1 to 3 wt %, in particular from 0.5 to 2 wt %, each based the total weight of the agent, is a further subject of the present invention.

Another subject of the present invention is the method previously recited for manufacturing a ketone according to the present invention of general formula (I), comprising the steps of:

a) producing organoborane adducts by hydroboration of a compound according to general formula (III)

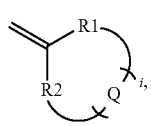

formula (III)

wherein i=1 or 2; R1 and R2 are each mutually and independently a secondary, tertiary, or quaternary carbon atom; and Q is at least one divalent substituted or unsubstituted group having 1 to 10 carbon atoms and bridging R1 and R2, and b) reacting the organoborane adducts generated in step a) with a compound according to general formula (IV)

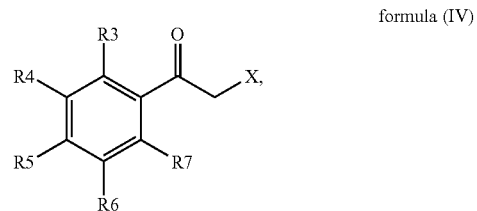

formula (IV)

wherein X is a halogen atom; and R3, R4, R5, R6, and R7 are mutually and independently hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms thereby producing a compound according to general formula (I).

In a particularly preferred embodiment of the aforesaid method, X in general formula (IV) is —Cl or —Br, particularly —Br. In a likewise preferred embodiment of the aforesaid method, four of the five aryl substituents R3, R4, R5, R6, and R7 in general formula (IV) are preferably hydrogen. R3, R4, R6, and R7 preferably are hydrogen, while the substituent in the R5 para-position is a halogen atom, $NO_2$, a linear or branched, substituted or unsubstituted alkoxy group having 1 to 15 carbon atoms, or a linear or branched, substituted or unsubstituted alkyl group having 1 to 15 carbon atoms. In a greatly preferred embodiment of the invention, R5 is —Cl, —Br, —$NO_2$, or an alkyl or alkoxy group encompassing 1 to 4 carbon atoms. By preference, the linear or branched, substituted or unsubstituted alkyl group is a methyl or ethyl group, and/or the linear or branched, substituted or unsubstituted alkoxy group is a methoxy, ethoxy, isopropoxy, or tert-butoxy group. The term "hydroboration" is to be understood for purposes of the invention as 1,2-addition of an organoborane reagent to at least one semicyclic double bond of the compound of the general formula (III), with the result that a covalent carbon-boron bond, and thus an organoborane adduct, is formed between the exocyclic Cβ atom of the semicyclic double bond and the boron atom of the organoborane reagent that is used. Suitable methods for hydroboration are described in J. March, Advanced Organic Chemistry, 4th Ed., pp. 783-789, to which reference is made here.

Hydroboration is preferably carried in a solvent. Suitable solvents for hydroboration include acyclic ethers such as diethyl ether, methyl tert-butyl ether, dimethoxyethane, diethylene glycol dimethyl ether, triethylene glycol dimethyl ether, cyclic ethers such as tetrahydrofuran or dioxan, and hydrocarbons such as hexane or toluene, or mixtures thereof. The reaction temperature is determined as a rule by the reactivity of the hydroboration agent, and is preferably between the melting and boiling points of the reaction mixture. In particular, the reaction can be carried out in THF and/or diethyl ether at temperatures from −100° C. to 40° C., preferably from −40° C. to 30° C., and particularly from 0° C. to 20° C. Suitable organoborane reagents include sterically demanding organoborane reagents. These can be selected, for example, from 9-borabicyclo[3.3.1]nonane (9-BBN), 1,1,2-trimethylpropylborane (thexylborane), catecholborane, or diisopinocampheylborane (lpc2BH). The organoborane reagent is preferably used in equimolar fashion or at an excess with reference to the at least one semicyclic double bond of the compound of the general formula (III). An advantage of the aforesaid method is the fact that the organoboron adducts that form preferably do not need to be isolated, but can be reacted directly, without previous purification, with a compound of the general formula (IV). The aforesaid reaction of the organoborane adduct with the compound of the general formula (IV) is accomplished by preference in a suitable solvent, for example, in acyclic ethers such as diethyl ether, methyl tert-butyl ether, dimethoxyethane, diethylene glycol dimethyl ether, triethylene glycol dimethyl ether, in cyclic ethers such as tetrahydrofuran or dioxan, and in hydrocarbons such as hexane or toluene, or in mixtures thereof. The above-described reaction can be carried out in greatly preferred fashion in the presence of an alkali metal alcoholate. Reaction temperature is determined by reactivity of the compound of general formula (IV) and/or by reactivity of the organoboron adducts, and is preferably between the melting and boiling points of the reaction mixture. In particular, the reaction can be carried out in THF and/or diethyl ether at temperatures between −100° C. and 40° C., by preference between −90° C. and 0° C., and in particular between −78° C. and −40° C.

In a greatly preferred embodiment, the aforesaid alkali metal alcoholate is chosen from potassium methanolate, sodium methanolate, potassium ethanolate, sodium ethanolate, potassium propylate, sodium propylate, potassium tert-butanolate, sodium tert-butanolate, potassium 2,6-di-tert-butylphenolate, sodium 2,6-di-tert-butylphenolate, and from any mixtures thereof. The alkali metal alcoholate is preferably used in equimolar fashion or at a slight excess (1.05 to 1.30 eq.) with respect to the organoborane adduct that is formed.

Purification of the ketone of general formula (I) that is formed is accomplished preferably by crystallization, distillation, and/or column chromatography. An advantage of the above-described manufacturing method is the fact that ketones of the general formula (I) can be manufactured, directly and economically, in a single-step convergent synthesis without laborious protecting-group operations. What results is a scent storage substance AB made up substantially of a photoreceptor (A) and a cyclic alkene having a semicyclic double bond (B). Irradiation then causes the aforesaid scent storage substance AB to decompose again without difficulty into its individual constituents A and B.

EXEMPLIFYING EMBODIMENTS

Example 1

Preparation of a Ketone According to General Formula (I)

Synthesis of 3-(6,6-dimethylbicyclo[3.1.1]-heptan-2-yl)-1-phenylpropan-1-one

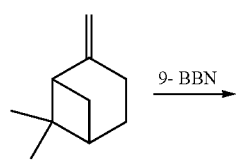

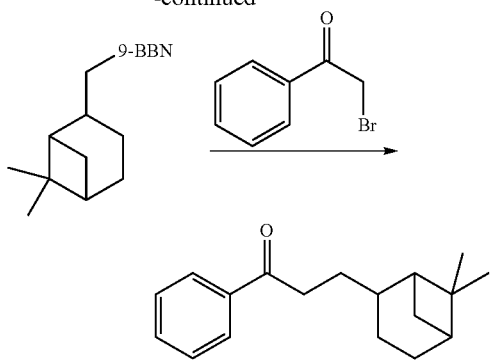

1.36 g (−)-β-pinene (10 mmol) was dissolved in 5 ml THF. 21 ml of a 0.5-molar solution of 9-BBN in THF (10.5 mmol) was added to this solution at 0° C. The reaction mixture was slowly brought to room temperature and stirred for a further 3 hours. The resulting solution was cooled to −78° C., and a solution of 1.12 g potassium tert-butanolate (10 mmol) in 10 ml THF was then added to the cooled reaction solution. After a short time, 2 g α-bromacetophenone (10 mmol) was added in portions with constant stirring. The reaction mixture was slowly brought to room temperature and stirred for 4 hours at room temperature. The resulting product mixture had 50 ml n-pentane added to it, and washed three times in each case with 10 ml of a 3N sodium hydroxide solution and with 10 ml water. The organic phase was dried over magnesium sulfate. Solvent was removed from the filtrate at reduced pressure. The raw product was purified by column chromatography. 140 mg (10%) of the aforesaid product was obtained.

Analytical Data:

Rf=0.75 (petroleum ether:ether=9:1)

$^1$H NMR (300 MHz, CDCl$_3$) (δ, ppm): 1.03 (s, 3H), 1.19 (s, 3H), 1.76-2.10 (m, 8H), 2.34 (q, 1H, 7.2 Hz), 2.95 (t, 2H, 8.1 Hz), 7.46 (t, 2H, 7.8 Hz), 7.55 (t, 1H, 7.2 Hz), 7.96 (d, 2H, 8.1 Hz);

$^{13}$C NMR (75 MHz, CDCl$_3$) (δ, ppm): 22.4, 23.3, 26.5, 28.2, 32.0, 33.8, 37.3, 38.7, 41.3, 41.5, 46.2, 128.1, 128.5, 132.8, 137.1, 200.8;

GC/MS (50-300M), m/z: 256, 238, 223, 195, 133, 119, 105, 91, 77, 55, 41.

Example 2

Exposing 3-(6,6-dimethylbicyclo[3.1.1]-heptan-2-yl)-1-phenylpropan-1-one to Light 20 mg 3-(6,6-dimethylbicyclo[3.1.1]-heptan-2-yl)-1-phenylpropan-1-one was dissolved in 8 ml methanol. The reaction solution was exposed in a multiple-lamp photoreactor (8 W lamps×4, Luxchem) with an emission maximum λ=350 nm for one hour. The reaction was followed using GC/MS spectrometry. After at most 60 minutes of exposure, the largely complete conversion of 3-(6,6-dimethylbicyclo [3.1.1]-heptan-2-yl)-1-phenylpropan-1-one into acetophenone and β-pinene was observed.

Example 3

Odor Test

For the odor test described below, 0.2 mmol 3-(6,6-dimethylbicyclo[3.1.1]-heptan-2-yl)-1-phenylpropan-1-one (photocaged pinene) was dissolved in 1 ml acetone. An odor strip was immersed to a depth of 2 cm in the solution, and then dried in the absence of light at 20° C.

For comparison, solutions of 0.1 mmol beta-pinene and 0.1 mmol acetophenone each in 1 ml acetone, and a mixture of 0.1 mmol beta-pinene and 0.1 mmol acetophenone in 1 ml acetone, were prepared. An odor strip was then immersed to a depth of 2 cm in each solution, and each odor strip was then dried at 20° C. in the absence of light.

After successful drying, each odor strip was irradiated over the entire testing time period with a commercial fluorescent tube (neutral white [NW] per DIN 5035; color temperature 3300 to 5500 K), and the scent intensity was determined at the respective times indicated.

The scent intensity was evaluated by three trained testers on a scale from 0 to 6, 6 being the highest score and 0 denoting no scent perceived.

Definition of Scoring Scale:
6 unpleasantly strong
5 very strong
4 strong
3 intense
2 pleasant
1 perceptible
0 no longer perceptible The results of the odor test are presented in the table below. The values indicated reflect the range of odor perception of the tester group.

|  | after 1 minute | after 20 minutes | after 45 minutes | after 1.5 hours | after 24 hours |
|---|---|---|---|---|---|
| photocaged pinene | strong chemical smell of acetophenone 1 | 0-1 | 0-1 | 0 can be smelled again with use of daylight lamp 0-1 | 0 can be smelled again with use of daylight lamp 0-1 |
| acetophenone | 3 | 3 | 2-3 | 2 | 0 |
| beta-pinene | 0-1 | 0 | 0 | 0 | 0 |
| acetophenone/ beta-pinene | only acetophenone perceptible 2-3 | 2-3 | 2 | 2 | 0 |

From the above it is seen that approximately 1 minute of irradiation with a 20 watt daylight lamp (LifeLite Full Spectrum Daylight Lamp) produces, even after 24 hours, photo-induced release of the pinene odor compound.

We claim:

1. Ketone according to the general formula (I)

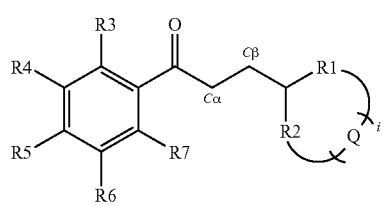

formula (I)

wherein i=1 or 2,

R3, R4, R5, R6, and R7 are each mutually and independently hydrogen, a halogen atom, NO₂, a linear or branched, substituted or unsubstituted alkoxy group having 1 to 15 carbon atoms, or a linear or branched, substituted or unsubstituted alkyl group having 1 to 15 carbon atoms, and R1 and R2 are each mutually and independently a secondary, tertiary, or quaternary carbon atom, and Q is at least one divalent substituted or unsubstituted group having 1 to 10 carbon atoms and bridging R1 and R2, wherein by cleavage of the Cα-Cβ bond, a ketone according to general formula (II)

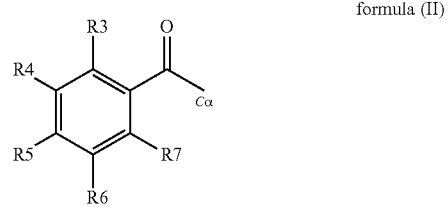

formula (II)

and a compound according to general formula (III)

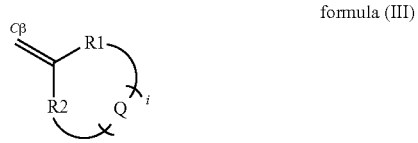

formula (III)

are formed, wherein i, R1, R2, R3, R4, R5, R6, R7, and Q have the meanings indicated above, wherein the compound of general formula (III) is a cyclic terpene or cyclic terpenoid having a semicyclic double bond, and wherein the cyclic terpene or cyclic terpenoid is chosen from β-phellandrene (p-mentha-1(7),2-diene), α-fenchene (7,7-dimethyl-2-methylenebicyclo[2.2.1]heptane), β-fenchene (2,2-dimethyl-5-methylenebicyclo-[2.2.1]heptane), camphene (2,2-dimethyl-3-methylenebicyclo[2.2.1]heptane), sabinene (4-methylene-1-(1-methylethyl)bicyclo-[3.1.0]hexane), pinocarveol, β-pinene (6,6-dimethyl-2-methylenebicyclo-[3.1.1]heptane), trichodiene (1,4-dimethyl-4-(1-methyl-2-methylenecyclopentyl)cyclohexene), β-humulene ((1E, 5E)-1,4,4-trimethyl-8-methylenecycloundeca-1,5-diene), or γ-humulene ((1E,6E)-1,8,8-trimethyl-5-methylenecycloundeca-1,6-diene), or from enantiomers and/or diastereomers thereof.

2. Ketone according to claim 1 wherein i=2 and at least one of the two bridging groups Q comprises 2 to 6 carbon atoms.

3. Ketone according to claim 1 wherein R1 and/or R2 and/or at least one divalent group Q bridging R1 and R2 is substituted with at least one heteroatom chosen from N, O, or S.

4. Ketone according to claim 1 wherein four of the five aryl substituents R3, R4, R5, R6, and R7 are hydrogen.

5. Ketone according to claim 1 wherein R3, R4, R5, R6, and R7 are hydrogen.

6. Textile- or surface-treatment agent comprising at least one ketone according to formula (I) of claim 1 in an amount of from 0.001 to 5 wt %, based on total amount of the agent.

7. Agent according to claim 6 further comprising at least one surfactant chosen from anionic, cationic, nonionic, zwitterionic, amphoteric surfactants, or mixtures thereof.

8. Agent according to claim 6 wherein the textile- or surface-treatment agent exists in solid form or in liquid form.

9. Cosmetic agent for treating skin and hair comprising at least one ketone according to formula (I) of claim 1 present in an amount of from 0.001 to 5 wt %, based on total amount of the agent.

10. Method for long-lasting scenting of surfaces comprising applying a ketone according to formula (I) of claim 1 onto a surface to be scented, and exposing the surface to electromagnetic radiation comprising wavelengths in a range from 200 to 400 nm.

11. Method for manufacturing a ketone of general formula (I) according to claim 1, comprising the steps of:
   a) Producing organoborane adducts by hydroboration of a compound of general formula (III)

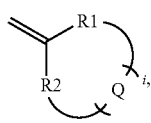

formula (III)

wherein i=1 or 2; R1 and R2 are each mutually and independently a secondary, tertiary, or quaternary carbon atom; and Q is at least one divalent substituted or unsubstituted group having 1 to 10 carbon atoms and bridging R1 and R2, and
   b) reacting the organoborane adducts generated in step a) with a compound of the general formula (IV)

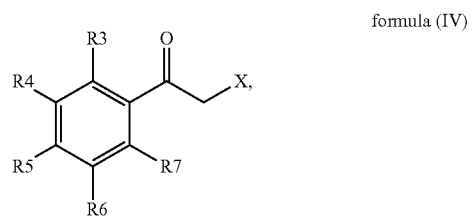

formula (IV)

wherein X is a halogen atom; and R3, R4, R5, R6, and R7 are each mutually and independently hydrogen, a halogen atom, $NO_2$, a linear or branched, substituted or unsubstituted alkoxy group having 1 to 15 carbon atoms, or a linear or branched, substituted or unsubstituted alkyl group having 1 to 15 carbon atoms,
   thereby producing a compound according to general formula (I).

* * * * *